US00PP32702P2

(12) United States Plant Patent
Brown et al.

(10) Patent No.: US PP32,702 P2
(45) Date of Patent: Dec. 29, 2020

(54) APPLE TREE NAMED 'NY73'

(50) Latin Name: ***Malus* x *domestica***
Varietal Denomination: NY73

(71) Applicant: CORNELL UNIVERSITY, Ithaca, NY (US)

(72) Inventors: Susan K. Brown, Geneva, NY (US); Kevin Maloney, Newark, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 16/602,082

(22) Filed: Aug. 1, 2019

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 5/0875
See application file for complete search history.

*Primary Examiner* — Kent L Bell
(74) *Attorney, Agent, or Firm* — Troutman Pepper Hamilton Sanders LLP (Rochester)

(57) ABSTRACT

A new and distinctive variety of a *Malus* x *domestica* apple tree named 'NY73', particularly characterized by its attractive fruit appearance, unique pink blush, overall superior horticultural performance and consistency, including excellent fruit quality at harvest by having firm, crisp, juicy, and flavorful fruit with great potential for marketing as both a fresh apple and in u-pick, retail, and wholesale operations is disclosed.

6 Drawing Sheets

FIELD

A new and distinct variety of apple tree designated as 'NY73'. The plant is botanically known as *Malus* x *domestica.*

BACKGROUND

Apples are an economically important crop both domestically and internationally. There is a growing need to develop new varieties of apple trees with improved characteristics to meet the changing needs and demands of the producer, processor, and consumer.

BRIEF SUMMARY

Disclosed is an improved variety of apple tree. In particular, a new and distinct variety of apple tree (*Malus* x *domestica*), which has been denominated as 'NY73'. The new variety 'NY73' has early maturity, is crisp, juicy, and has good flavor, with a balance of sweetness, acidity, and aromatics. The fruit are firm, large size, and unique in appearance with a bright pink blush color and light green background color, and overall attractive appearance. The fruit have multiple market uses. The fruit can be used for fresh consumption, in cooking, are suited to u-pick, retail, and wholesale markets, and in processing as part of a blended product.

'NY73' was selected for its excellent appearance (with a unique pink blush), quality attributes (crispness, juiciness, flavor, firmness), large size, and overall horticultural performance and consistency.

Apple tree 'NY73' is a hybrid that originated from a planned controlled cross in 1997 in Geneva, N.Y. The seed parent (female parent) is *Malus* x *domestica* 'Imperial Gala' apple tree (unpatented). The pollen parent (male parent) is *Malus* x *domestica* 'Honeycrisp' apple tree (U.S. Plant Pat. No. 7,197).

The original cross, designated '733', was made by applying pollen from a 'Honeycrisp' apple tree onto emasculated flowers of an 'Imperial Gala' apple tree in Geneva, N.Y. in 1997. Seedlings were planted on their own roots in an orchard in Geneva, N.Y. in 1998, after being stratified and grown in the greenhouse. One seedling, designated NY97733-73, was selected from a field population of 331 seedlings on the basis of excellent fruit quality, firm flesh, and unique and attractive fruits. Additional trees of seedling NY97733-73 were produced by clonal propagation starting in 2002 and in subsequent years in Geneva, N.Y. These additional trees were evaluated for fruit and tree characteristics, pest resistance, and trueness-to-type. NY97733-73 was later designated as 'NY73'.

'NY73' was first asexually (clonally) propagated by chip budding onto apple tree rootstock 'M.9' (unpatented) in 2002 in a research nursery in Geneva, N.Y. Subsequent asexual reproduction of 'NY73' has been successful using traditional grafting and budding methods of propagation, demonstrating that the unique combination of traits of the asexually propagated trees is identical in all appearances to the original tree. Asexual reproduction of this new variety by grafting and budding onto rootstocks shows that the characteristics of asexually propagated trees are true-to-type and are established and transmitted through succeeding propagations.

Distinguishing Characteristics of 'NY73'

Seed Parent: The seed parent *Malus* x *domestica* 'Imperial Gala' is a sport of 'Gala' (U.S. Plant Pat. No. 3,637). 'Gala' and its colored sports are known for their fruit quality, characterized by having fruit with a spicy, sweet flavor. Bi-color fruit have a mixture of both red blush and stripes and a green/yellow background color, and a firm and juicy fruit texture with mostly smooth skin. Occasional russeting of the stem cavity and lenticels may occur. When compared to 'Imperial Gala', 'NY73' has similar scion vigor and tree characteristics. 'NY73' has similar fruit quality characteristics to 'Imperial Gala' in its firm texture. However, 'NY73' produces fruit that have larger fruit size and a pink/red blush color compared to the red blush/stripe of 'Imperial Gala'.

Pollen Parent: The pollen parent 'Honeycrisp' is an internationally grown and recognized variety. When compared to 'NY73', the pollen parent 'Honeycrisp' produces fruit that have similar large size, but have a globose shape compared to the globose-conical shape of 'NY73'. 'NY73' has a pink/red blush over-color compared to the less colored, lighter-red 'Honeycrisp' fruit. 'NY73' has greater scion vigor compared to the weaker growth habit of 'Honeycrisp'. The texture and juiciness of 'NY73' are similar to its 'Honeycrisp' parent.

'NY73' has earlier fruit maturity, larger fruit size, lighter surface color, and a milder flavor compared to the commercial variety 'Empire'. 'Empire' was introduced in 1966 and is not patented. The commercial variety 'New York 2' (Ruby Frost, U.S. Plant Pat. No. 22,207) has more full red color, globose fruit shape, and later fruit maturity compared to 'NY73' having a taller globose-conical fruit shape and lighter skin coloring. 'New York 2' has more acidity. Both 'New York 2' and 'NY73' have resistance to flesh browning after the fruits are cut.

BRIEF DESCRIPTIONS OF THE DRAWINGS

The accompanying images illustrate characteristics of 'NY73'. The colors shown are as true as can be obtained reasonably by conventional photographic procedures. However, the colors in the images may vary with lighting conditions and, therefore, color characteristics of this new variety should be determined with reference to the observations described herein, rather than from the photographs alone. The photographs are from trees that are 18-years-old for FIG. 1, and from trees that are 10-years-old for FIG. 2 to FIG. 6.

Figure 1:
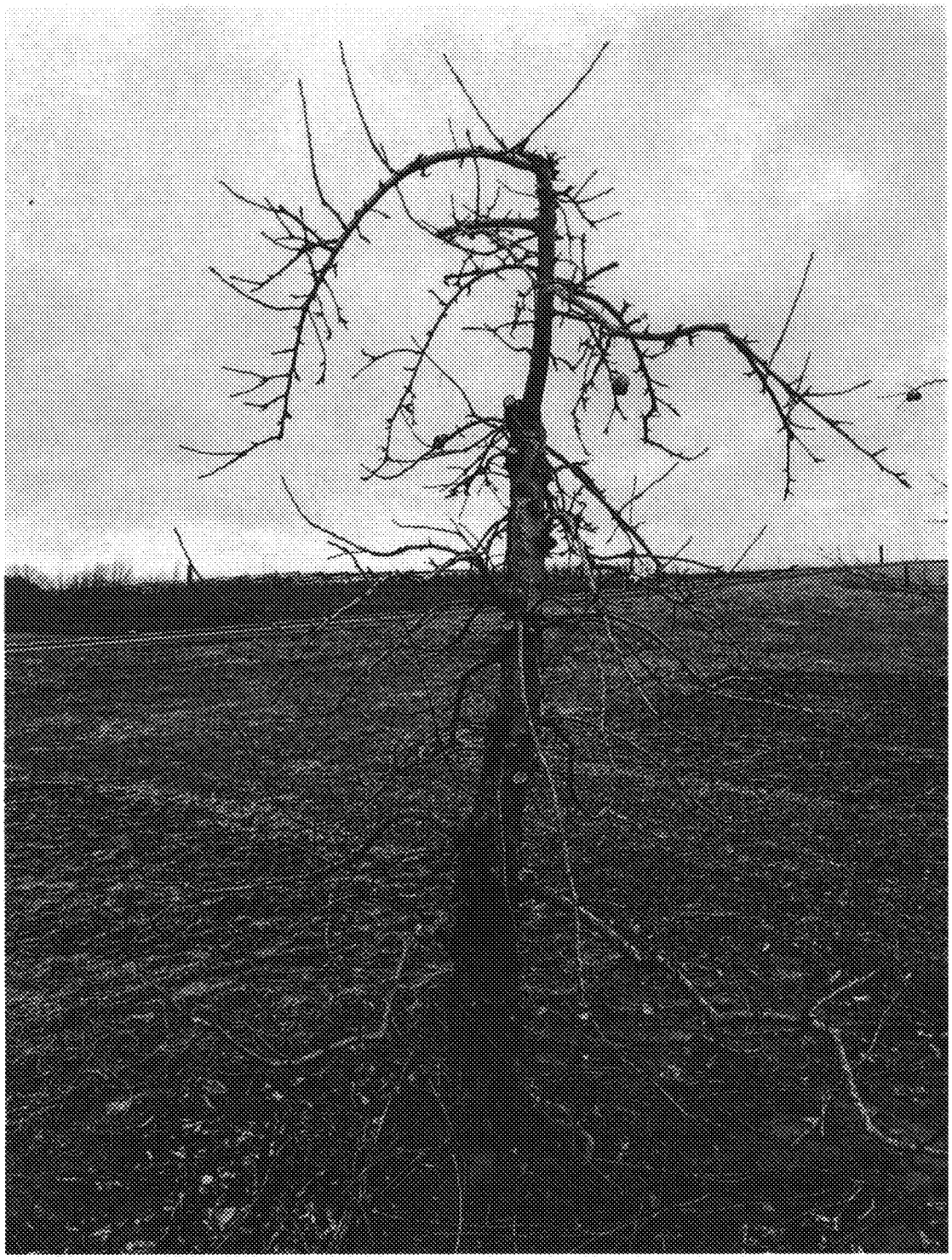
FIG. 1 depicts the original, dormant, free-standing seedling tree of apple tree variety 'NY73'.
Figure 2:
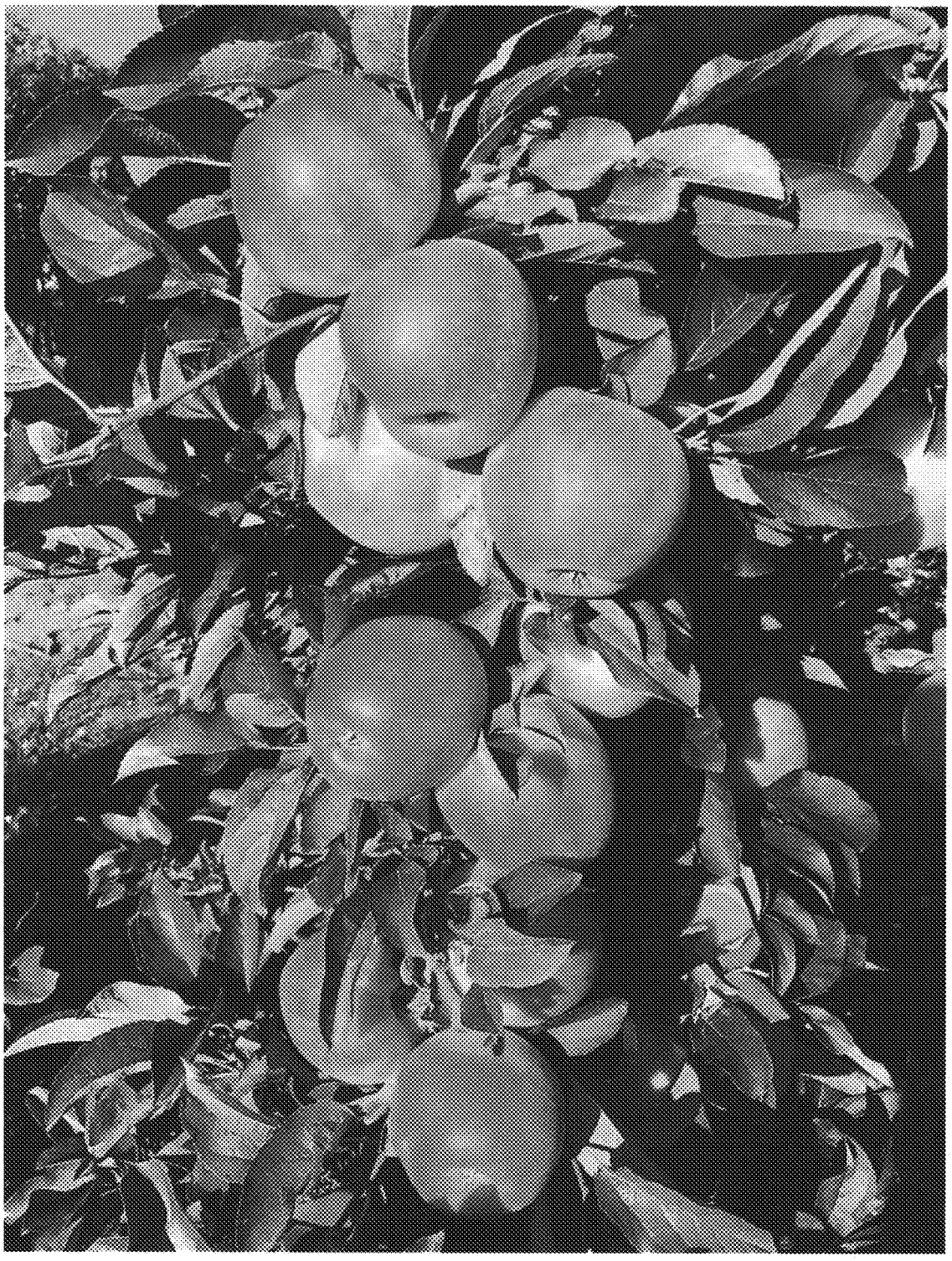
FIG. 2 depicts a close up of fruit of apple tree variety 'NY73' at harvest.
Figure 3:
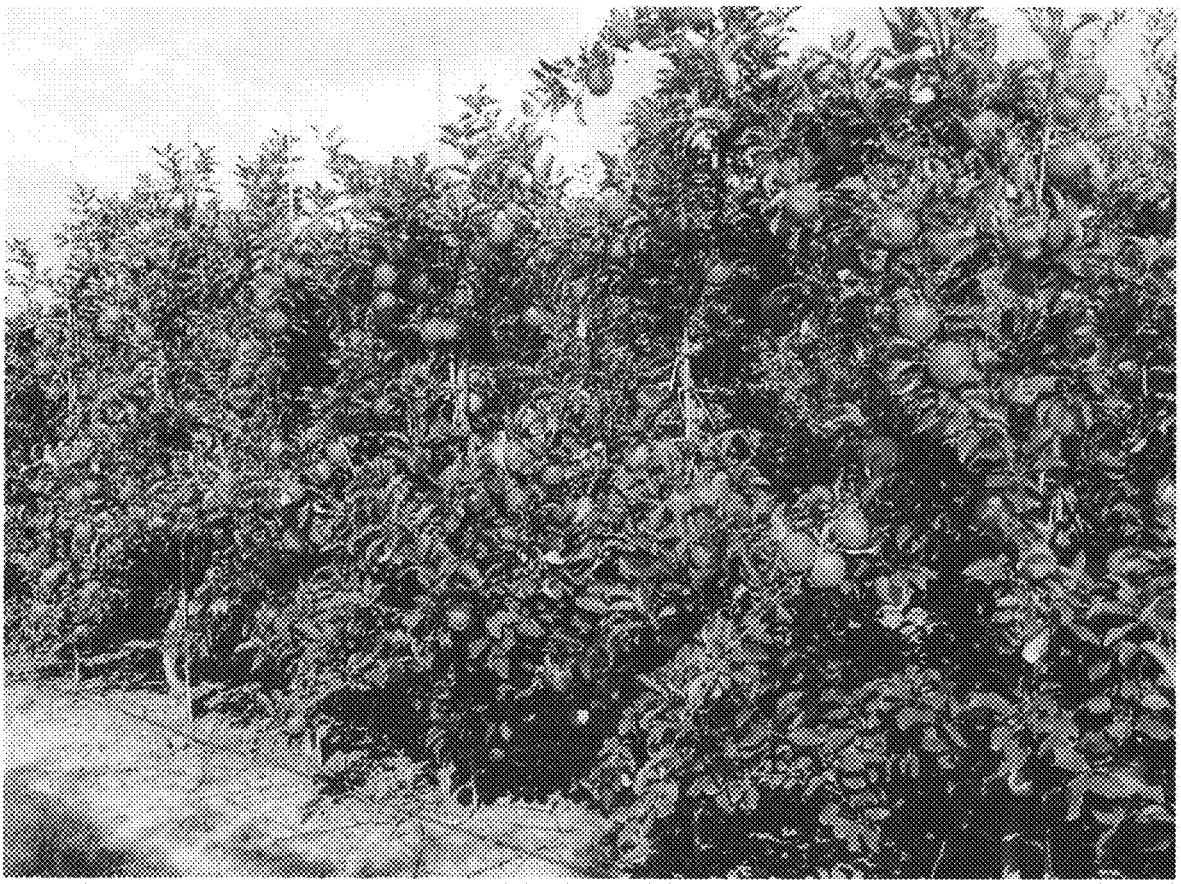
FIG. 3 depicts a row of trees of apple tree variety 'NY73' in orchard.
Figure 4:
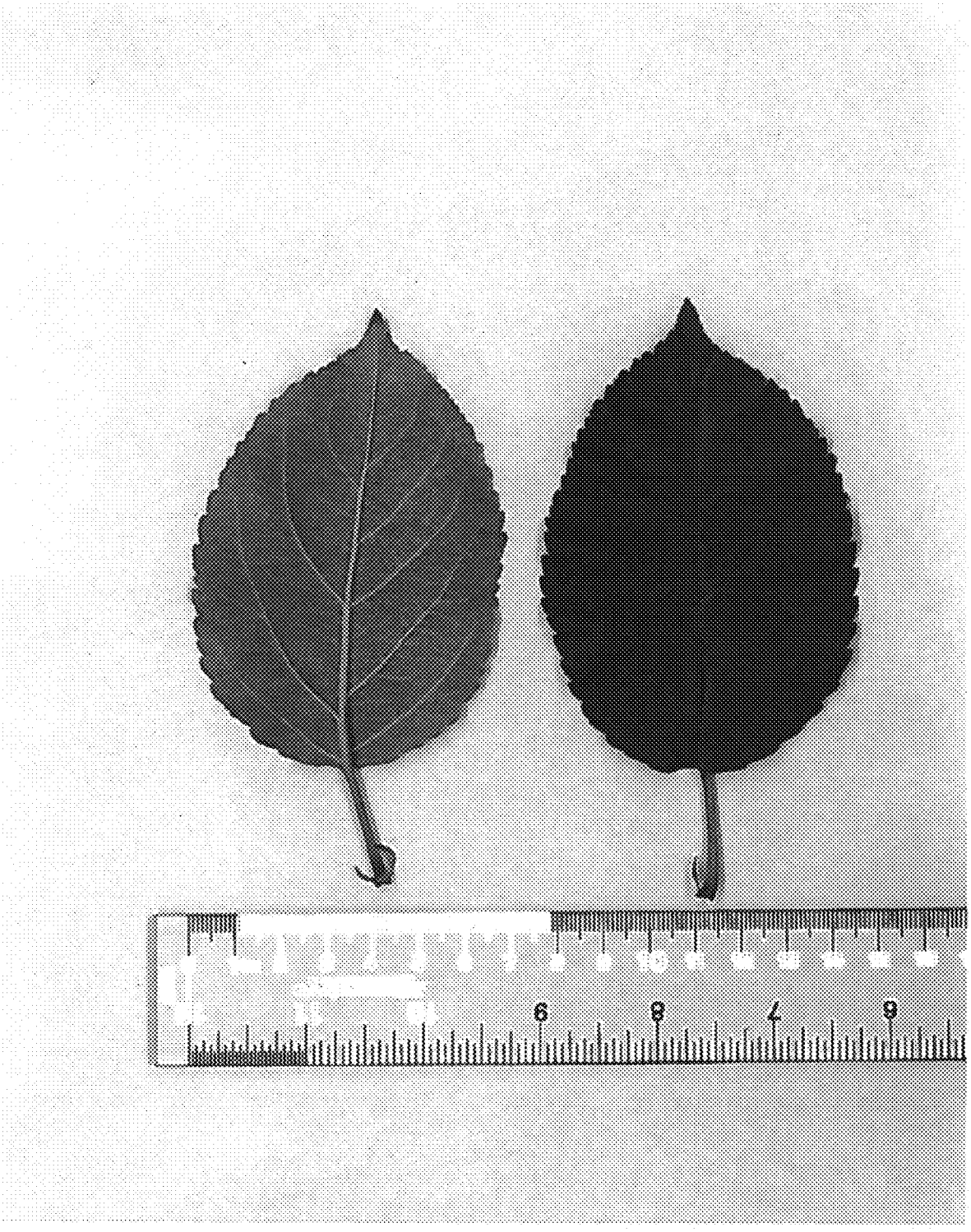
FIG. 4 depicts both an upper and lower surface of a mature leaf of apple tree variety 'NY73'.
Figure 5:
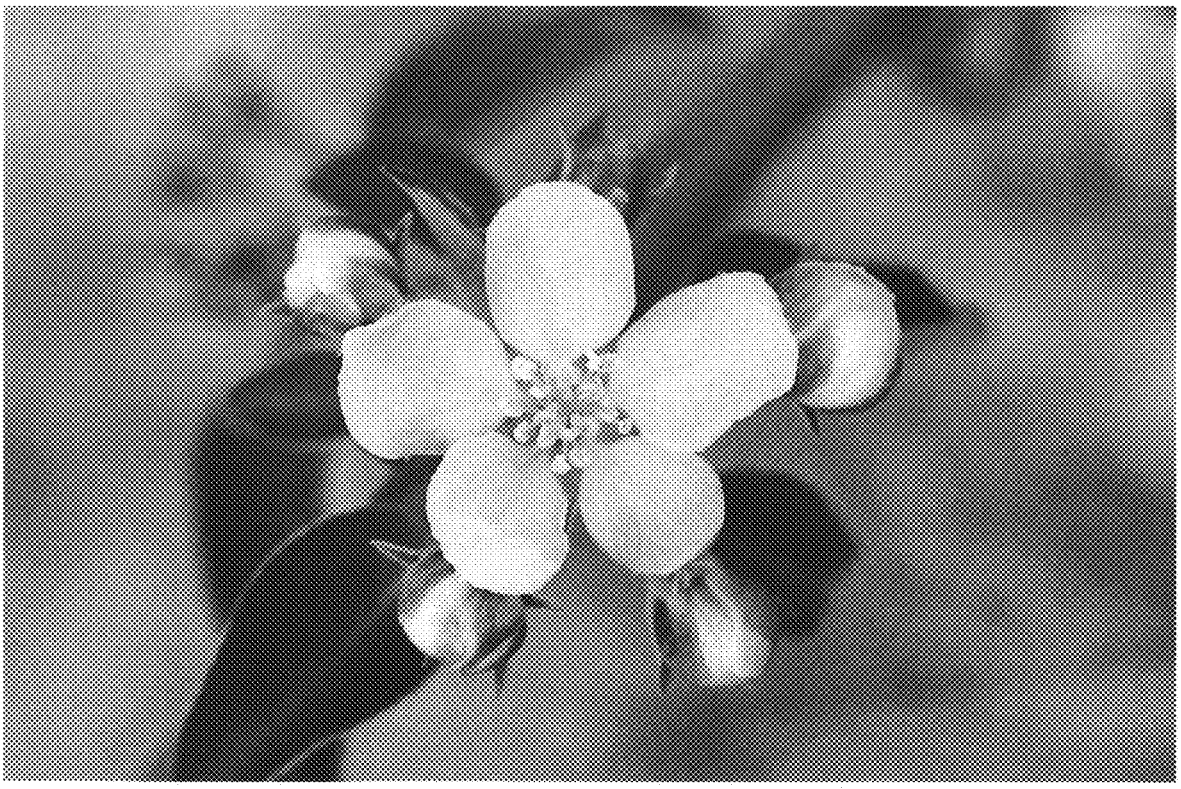
FIG. 5 depicts a flower cluster of apple tree variety 'NY73'.
Figure 6:
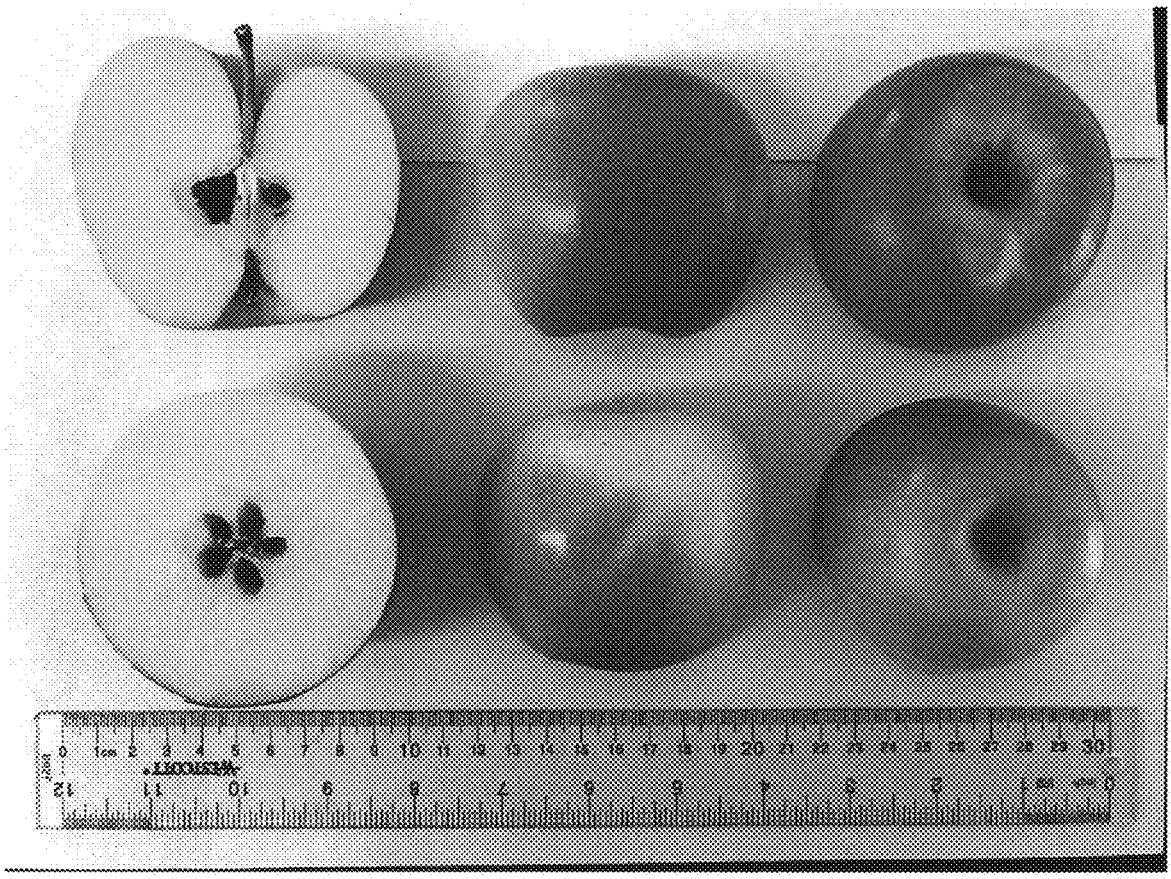

FIG. 6 depicts six views of a typical fruit of apple tree variety 'NY73'. The fruit at the top left depicts a cross section of 'NY73' fruit cut longitudinally from top to bottom. The fruit at the top middle depicts a side view of the sun-exposed side of 'NY73' fruit. The fruit at the top right depicts a stem and stem cavity of 'NY73' fruit. The fruit at the bottom left depicts a cross section of 'NY73' fruit cut horizontally through the seed cavity. The fruit at the bottom middle depicts a side view of the shaded side of 'NY73' fruit. The fruit at the bottom right depicts a calyx and basin area of 'NY73' fruit.

DETAILED BOTANICAL DESCRIPTION

The following description sets forth the distinctive characteristics of apple tree 'NY73'. The following description is based on the originally identified apple tree and asexually reproduced progeny grown in Geneva, N.Y., which is in USDA Plant Hardiness Zone 6A.

Referring more specifically to the details of the new and distinct apple tree variety 'NY73', unless otherwise stated, the following observations and characteristics have been taken since 1999 from a number of trees in different orchards to provide consistent descriptions.

Certain characteristics of this variety may change with changing environmental conditions (e.g., light, temperature, moisture, etc.), nutrient availability, or other factors. Quantified measurements are expressed as an average of measurements taken from a number of individual plants of the new variety. The measurements of any individual plant, or any group of plants, of the new variety may vary from the stated average. Color descriptions and other terminology are used in accordance with their ordinary dictionary descriptions, unless the context clearly indicates otherwise. Color designations are made with reference to The Royal Horticultural Society Colour Chart (RHSCC) copyright 2001.

Tree: Medium in size; standard upright habit; medium vigor; early bearing on spurs. Trees are conducive to both free standing and trellis-supported production systems. Twelve-year-old managed trees have an average height of 3.1 m, spread of 2.0 m and average trunk diameter of 6.3 cm at 30 cm above the soil line. Approximate bud break is about April 15 in Geneva, N.Y.

Tree trunk: One-year-old dormant wood surface color is RHSCC Greyed-orange 166A. Four-year-old dormant wood surface color is RHSCC Grey-brown N199C and Greyed-orange 177B. Bark lenticels are medium, round to elongate in shape, average 4.6 per square centimeter, and range from 0.7 mm to 5.0 mm in length.

Branch: Branch diameter of four-year-old wood is 17.4 mm. Branch angle is flat, typically 0 degrees to 20 degrees above the horizontal. Thirteen-year-old trees propagated on M9 rootstock have on average 27 branches per tree, 19 mm average branch diameter, 89 cm average branch length, slightly rough texture, four-year-old branch color is RHSCC Greyed-orange 177B. Internode length of one-year-old branches averages 2.5 cm. Average spur length 8.3 cm, spur diameter 6.6 mm, color RHSCC Brown 200B and 3.2 average fruit buds per spur.

Leaf: Leaves are pinnately veined, alternate in arrangement and medium in size. Apex is convex, base is rounded. Average leaf blade length is 99 mm and average blade width is 68 mm. Concavo-convex in cross section; upward in pose; medium glossiness of upward (adaxial) side; serrate margin indentation; average 1.9 serrations per centimeter. Upper surface is smooth, lower surface has very fine pubescence. The color of the upper leaf blade surface is most similar to RHSCC Green 139A and the color of the upper veins is RHSCC Yellow-green 148B. The color of lower leaf blade surface is RHSCC Green N138D and the color of lower veins is RHSCC Yellow-green 148B. Leaf petioles are medium in length, with an average length of 27 mm and diameter 2.7 mm. The colors of the petiole are RHSCC Yellow-green 148C and the color of the tinged petiole base is RHSCC Greyed-red 178A. Stipules average 7.7 mm in length and 1.6 mm in width. Stipule color is RHSCC Green N138A.

Flower: Flower color at the "pink" phenology stage is RHSCC Greyed-purple 186C. Flower petals in open flower clusters are mostly meeting and slightly overlapping. Flower diameter averages 43 mm and flower height is 21 mm in open flowers. There are five petals per flower and petals are slightly cupped upward. Average petal length is 21.0 mm, average petal width is 14.3 mm. Flower petal color when open is RHSCC White 155B, with some petal veins showing a pink tinge (RHSCC Red-purple 64A). Both upper and lower petal surfaces are smooth. Petal shape is oval, apex rounded, base ovate, margin smooth and undulate. Flowers are self-sterile and require pollination by another diploid apple of a similar bloom timing. Approximate bloom time is May 7, lasting up to 7 days in Geneva, N.Y.

Flower pedicel color: RHSCC Yellow-green 147B. Length 17.2 mm, width 1.3 mm. Pedicel texture is smooth and finely pubescent.

Stamens: 20 stamens per flower, average 8.0 mm long and filament color is RHSCC Grey-green 195C. Anther color is RHSCC Greyed-yellow 162C, oval shape, 2 mm in length. Pollen color is RHSCC Yellow 11B, average general amount.

Style: Is 11.8 mm long. Style number is five per flower. Style color is RHSCC Yellow-green 152D. Stigma color is RHSCC Yellow-green 154D and rounded in shape. One pistil—imperfectly syncarpic. Ovary color is RHSCC Yellow-green 148C.

Sepals: Sepal color is RHSCC Green 138C. Sepal length is 8.2 mm, and sepal width is 3.9 mm. Five sepals per flower, deltoid shape, pointed apex, slightly reflexed, smooth margins, upper and lower surfaces both smooth with inconspicuous pubescence.

Fruit: Fruit examined at harvest time:

Soluble solids: Average 12.8° Brix, with a range of 11.0-16.5° Brix.

Acidity: 0.49% malic acid as determined by titration.

Juice pH: Average 3.7 (range 3.5-3.9).

Firmness: Average 17.9 pounds pressure (range 15.7-20.1 pounds) as measured with a penetrometer.

Shape: Mostly globose-conical.

Starch-iodine index ratings near maturity: Average 5.1 (range 3.4-6.3).

Weight: Average 209 grams (range 151-303 grams).

Fruit diameter: Average 8.1 cm (range 6.9-8.9 cm).

Height: Average 7.3 cm (range 6.1-8.2 cm).

Color: Darkest fruit skin over-color is RHSCC Red 46B; lighter fruit skin color is RHSCC Greyed-red 179B. Fruit background color is RHSCC Greyed-yellow 162B. Fruit over-color average is 60%, ranging from 20% to 90%. Fruit lenticels are mostly round, inconspicuous, RHSCC Grey-brown 199B and White155B in color. There is an average of 6.1 fruit skin lenticels per square centimeter.

Stem cavity: Acute, with a depth of 22.0 mm and a width of 27.8 mm. Stem cavity russet color is RHSCC Grey-brown 199D. Fine smooth russeting in the stem cavity, occasionally extends to the fruit shoulders.

Stem: Long (22.2 mm length) and thick (2.7 mm stem thickness). Fruit stem color is RHSCC Greyed-yellow 161A and Yellow-green 153B, tinged with Greyed-orange 163B.

Basin: Abrupt, medium to deep, medium breadth. Average basin depth 10.4 mm, average basin width 23.8 mm.

Calyx: Persistent, and closed, with lobes united at base.

Calyx tube: Conical shaped.

Stamen remnants: Basal.

Carpels: Roundish, axile and smooth. Individual carpels range from 6 to 9 mm in width and 20 to 27 mm in length.

Core position: Median and closed.

Core lines: Meeting, length 27 mm and width 33 mm.

Seeds: Five locules per fruit. Average 8.4 seeds per fruit. Seed length 7.8 mm; seed width 5.1 mm; seed depth 3.0 mm. Obtuse in shape. Fresh seed color RHSCC Brown 200B. Dried seed color RHSCC Grey-brown N199B.

Skin thickness: Medium thick 0.31 mm. Skin: smooth, slight bloom, non-greasy.

Flesh: Fruit flesh color is RHSCC White155B.

Texture: Crisp and firm.

Flavor: The flavor is sweet and mild with light acid and aromatics.

Harvest time: Maturity ranges between September 8 (first pick) and September 18 (last pick) in Geneva, N.Y.

Use: Fresh, juice, multiple use.

Keeping quality: 70 days with minimal or no disorders.

General culture: Apple tree variety 'NY73' is considered as susceptible, but not more susceptible, as most other apple varieties to all insects, diseases, and climate-related disorders found in apple production regions of New York. 'NY73' fruit held in cold storage after harvest are susceptible to certain storage disorders, their occurrence increases with time in storage and is variable and influenced by the year.

Production & management: 'NY73' can be grown on many rootstocks in both trellised and free-standing systems. 'NY73' can be managed and pruned similar to other commercially available apple varieties. Trees require standard management for optimum tree growth and fruit quality. Trees require fertilization, fruit thinning for crop load management, pest control, and dormant pruning.

What is claimed:

1. A new and distinct variety of apple tree named 'NY73' as herein described and illustrated.

* * * * *